United States Patent [19]

Kawada

[11] Patent Number: 6,037,371
[45] Date of Patent: Mar. 14, 2000

[54] INSECTICIDAL/ACARICIDAL COMPOSITION

[75] Inventor: Hitoshi Kawada, Funabashi, Japan

[73] Assignee: Sumitomo Chemical Company, Limited, Osaka, Japan

[21] Appl. No.: 09/154,580

[22] Filed: Sep. 17, 1998

[30] Foreign Application Priority Data

Sep. 26, 1997 [JP] Japan .................................. 9-261718

[51] Int. Cl.$^7$ ............................ A01N 37/44; A01N 43/38
[52] U.S. Cl. ............................ 514/535; 514/411; 514/537
[58] Field of Search ..................... 514/535, 537, 514/411

[56] References Cited

U.S. PATENT DOCUMENTS 5,698,591  12/1997  Mori et al. .............................. 514/535

FOREIGN PATENT DOCUMENTS 57-156407   9/1982   Japan .
8-319202   12/1996   Japan .

OTHER PUBLICATIONS

The Pesticide Manual Incorporating the Agrochemical Handbook, Editor Clive Tomlin, p. 392 10$^{th}$ Ed (1994).

Primary Examiner—Allen J. Robinson
Attorney, Agent, or Firm—Birch, Stewart, Kolasch & Birch, LLP

[57] ABSTRACT

An insecticidal/acaricidal composition which comprises 2-methoxycarbonyl-4-chlorotrifluoromethanesulfonanilide and N-(2-ethylhexyl)bicyclo[2.2.1]hept-5-ene-2,3-dicarboximide as an active ingredient, and inert carrier is useful for controlling insects/acarina effectively.

6 Claims, No Drawings

INSECTICIDAL/ACARICIDAL COMPOSITION

FIELD OF INVENTION

The present invention relates to an insecticidal/acaricidal composition which is particularly suitable for controlling mites and/or ticks.

BACKGROUND ART(S)

Mites and/or ticks have been a nuisance to many people and have often been considered noxious pests. In an attempt to control the population of these mites and/or ticks, insecticidal/acaricidal compositions have been developed. 2-methoxycarbonyl-4-chlorotrifluoromethanesulfonanilide, shown with its chemical structure below:

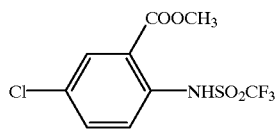

is known as an active ingredient of an insecticidal/acaricidal composition, based upon Japanese Laid-open Patent Nos. sho-57-156407-A and hei-8-319202-A.

N-(2-ethylhexyl)bicyclo[2.2.1]hept-5-ene-2,3-dicarboximide, widely known as MGK-264, noted as a compound in "The Pesticide Manual 10th ed." page 392 (published by British Crop Protection), is also known for its utilization as a synergist (as itself, it shows no insecticide abilities, but strengthens its lethality when it is added to allethrin) when mixed with allethrin. Recently, with the emergence of the high activity of the pyrethroid compound replacing allethrin, a new to service with N-(2-ethylhexyl) bicyclo [2.2.1]hept-5-en-2,3-dicarboxyimide other than additive substance to allethrin was hoped to be engineered. (cf. "Nouyaku no seiyukikagaku to bunshisekkei (Bioorganic Chemistry and Molecular Design of Pesticides)" editted by Kazufusa Eto, published by Soft Science Co. (1985))

The insecticidal/acaricidal compositions developed to the point, however, cannot effectively control mite and/or ticks. It would be of advantage, to have an insecticidal/acaricidal composition that can effectively control noxious pests such as indoor inhabiting mites.

DISCLOSURE OF INVENTION

The present invention is an attempt to provide an insecticidal/acaricidal composition having its insect and/or acarina killing effectiveness.

According to the present invention, if an insecticidal/acaricidal composition comprised of 2-methoxycarbonyl-4-chlorotrifluoromethanesulfonanilide and N-(2-ethylhexyl)-bicyclo [2.2.1]hept-5-ene-2,3-dicarboximide; the present insecticidal/acaricidal composition will exhibit insect and/or acarina killing effectiveness.

The insecticidal/acaricidal composition of the present invention is a composition containing 2-methoxycarbonyl-4-chlorotrifluoromethanesulfonanilide and N-(2-ethylhexyl) bicyclo[2.2.1]hept-5-ene-2,3-dicarboximide as its active ingredients; and within the insecticidal/acaricidal composition of the present invention, the 2-methoxycarbonyl-4-chlorotrifluoromethanesulfonanilide and N-(2-ethylhexyl) bicyclo[2 .2.1]hept-5-ene-2,3-dicarboximide, generally have a weight ratio inside the range of 1:1 to 1:50.

The insecticidal/acaricidal composition of the present invention generally; any carrier in addition to the active ingredients of 2-methoxycarbonyl-4-chlorotrifluoromethanesulfonanilide and N-(2-ethylhexyl) bicyclo[2.2.1]hept-5-ene-2,3-dicarboximide, if necessary, auxilaries for formulation such as a dispersing agent, wetting agent, adhesive agent, anti-oxidant, ultraviolet stabilizer and so on may be contained. The present composition takes a formulation of each variation such as oil formulation, emulsifiable concentrates, suspensible concentrates, dusts, granules, aerosol formulation, combustion agent, heated vaporization agent, a sheet formulation, and so on.

Usable carriers in the event of formulation, liquid carriers such as hydrocarbons (for example, toluene, xylene, methylnaphthalene, phenylxylylethane , kerosene, hexane, cyclohexane), ethers (for example, diethyl ether, ethylene glycol dimethyl ether, tetrahydrofuran, dioxane), ketones (for example, acetone, methyl ethyl ketone, methyl isobutyl ketone, cyclohexanone, isophorone), alcohols (for example, methanol, ethanol, isopropyl alcohol, hexanol, ethylene glycol), amides (for example, N,N-dimethylformamide, N,N-dimethylacetamide), and so on; and/or solid carriers such as talc, bentonite, clay, kaolin, diatomite, silica, vermiculite, perlite, and so on; may be contained. Furthermore, in the situation where the insecticidal/acaricidal composition of the present invention is formulated as an aerosol, gaseous carriers such as nitrogen, carbon dioxide, dimethyl ether, and LPGs may be contained to be a propellant.

In the situation where the insecticidal/acaricidal composition of the present invention, is an inflamable smoking formulation, a foaming agent may be contained in addition to the active ingredients. This foaming agent for example, may be illustrated by organic foaming agents such as azodicarbonamide, azobisisobutyronitrile, dinitropentamethylenetetramine, and/or p,p'-oxy-bis (benzenesulfonylhydrazide) and so on which can create nitrogen by heat decompose. In the situation of utilizing this inflamable smoking formulation, for example, the method stated in Japanese examined patent No. sho-59-49201-B where a container divided by a wall has granules for the smoking agent within it, calcium oxide within the other, then have water added to the calcium oxide at the time of use, then using the heat from the chemical reaction at that moment to exterminate acarina and/or insects is convenient.

However, in the situation where the insecticidal/acaricidal composition of the present invention is a combustable type smoking formulation, in addition to the effective components, standardly, potassium perchlorate, potassium nitrate, and potassium chlorate, and so on for the oxygen feeding agents; sugars, starches for the combustable agents; further, when needed, guanidine nitrate, nitroguanidine, dicyandiamide, guanylurea phosphate, and guanidine sulfamate, and so on for the heat-emitting control agents and/or potassium chloride, sodium chloride, iron (III) oxide (IV), copper oxidized, chromium oxidize, iron oxidize, iron chloride, active carbon and so on for the oxygen source-decomposition helping agents, perlite, diatomaceous earth, talc, clay, and so on for the inorganic carriers may be contained; and by mixing each of the listed components, added water and kneaded, formed to granules, and dried for a common standard method of production.

In the situation where the insecticidal/acaricidal composition of the present invention, is formulated as a mat formulation for vaporization under heating (in other words, a mosquito-mat formulation for electric heating), this insecticidal/acaricidal composition, has the active ingredients preserved in cotton linter, non-woven fabric, ceramic board, and/or thick paper and so on for porous carriers. This mat formulation for vaporization under heating is heated 100° to 300° C. and utilized for example, when using an electric mosquito-mat heater from the market.

In the situation where the insecticidal/acaricidal composition of the present invention takes a form of a sheet, as a sheet material, for example, paper, synthetic resin films such as polyolefins, polyesters, polyvinyl chlorides, etc., synthetic fibers, natural fibers such as wool, silk, cotton, and so on that are woven or moreover non-woven is used. With about 1 $m^2$ of this sheet material, standardly, 2-methoxycarbonyl-4-chlorotrifluoromethanesulfonanilide and N-(2-ethylhexyl)bicyclo[2.2.1]hept-5-ene-2,3-dicarboximide have a quantitative sum total of 0.01 to 2.00 g preserved. Furthermore, this sheet material standardly, uses a thickness of about 0.01 to 10 mm.

When the insecticidal/acaricidal composition of the present invention takes a form of a sheet; standardly, 2-methoxycarbonyl-4-chlorotrifluoromethanesulfonanilide and N-(2-ethylhexyl)bicyclo[2.2.1]hept-5-ene-2,3-dicarboximide with mixing components; furthermore, possible solutions (for example, ketone solvents such as acetone, alcohol solvents such as methanol, ester solvents such as ethyl acetate, halogenated hydrocarbon solvents dichloromethane, aromatic hydrocarbon solvents such as benzene, aliphatic hydrocarbon solvents such as hexane, and so on for components dissolved in organic solvents) may be soaked into the sheet material for production but; the synthetic resin film or synthetic fiber to become the sheet ingredient may, previously have 2-methoxycarbonyl-4-chlorotrifluoromethanesulfonanilide and N-(2-ethylhexyl)-bicyclo [2.2.1]hept-5-ene-2,3-dicarboximide with mixture components furthermore, possible solutions, integrated, and afterwards formed into a film and/or something woven as a fiber is feasible.

Rather, the insecticidal/acaricidal composition of the present invention is a composition that has 2-methoxycarbonyl-4-chlorotrifluoromethanesulfonanilide and N-(2-ethylhexyl)bicyclo[2.2.1]hept-5-ene-2,3-dicarboximide as active ingredients; but on the other hand, other insecticidal/acaricidal (for example, permethrin, empenthrin, etc. of the pyrethroid compounds), synergists, and/or bacteriocides/fungicides can be contained.

The insecticidal/acaricidal composition of the present invention; especially, indoor inhabiting mites, for example, Dermanyssidae such as American house dust mite (*Dermatophagoides farinae*), *Dermatophagoides pteronyssnus* and so on, Acaridae such as "kounohoshika" mite, copra mite (*Tyrophagus putrescentai*), brown legged grain mite (*Aleuroglyphus ovatus*), Glycyphagidae such as *Glycyphagus privatus, Glycyphagus domesticus, Glycyphagus destrutor* and so on, "marunikudani" mite, Cheyletidae such as *Chelacaropsis moorei, Chelacaropsis malaccensis, Cheyletus fortis*, "hosotsumedani" mite, "ashinagatsumedani" mite and so on, Macronyssidae such as *Ornithonyssus bacoti, Ornithonyssus sylviarum, Dermanyssus gallinae,* "suzumesashidani" mite and so on, Halpochthonius spp., Pyemotes spp., itch mite, and so on are effectively exterminated but, not only limited to these mites, fleas such as cat flea (*Ctenocephalides felis*), dog flea (*Ctenocephalides canis*) and so on, cockroaches such as German cockroach (*Blattella germanica*), smokybrown cockroaches (*Periplaneta fuliginosa*) and so on, Psocidae such as *Liposcelis bostrychophilus, Liposcelis entomophilus,* and so on, ants such as little red ant (*Monorium pharaonis*) and so on, bed bugs such as *Cinemex lectularius* and so on; is also effective to exterminate harmful insects.

EXAMPLES

Below, the present invention will be explained in detail by examples.

Production Example 1

Five parts by weight of 2-methoxycarbonyl-4-chlorotrifluoromethanesulfonanilide and 15 parts by weight of N-(2-ethylhexyl)bicyclo[2.2.1]hept-5-ene-2,3-dicarboximide, 0.5 part by weight of zinc oxide, and 2 parts by weight of α-starch were mixed with azodicarbonamide to make the complete body 100 parts by weight, then added water and kneaded, then formed to granules by an extrusion machine, then dried to gain the insecticidal/acaricidal composition of the present invention (smoking formulation).

Production Example 2

1.5 g of the mixture of 5 parts by weight of 2-methoxycarbonyl-4-chlorotrifluoromethanesulfonanilide and 15 parts by weight of N-(ethylhexyl)bicyclo[2.2.1]hept-5-ene-2,3-dicarboximide, 2.5 g of azodicarbonamide, 1.5 g of nitrocellulose, 0.4 g of dibutyl phthalate, 0.54 g of zinc oxide, 2.56 g of perlite, and 1.0 g of polyvinyl alcohol were combined, then added water and kneaded, then formed to granules by an extrusion machine, then dried to gain the insecticidal/acaricidal composition of the present invention (smoking formulation).

Production Example 3

One gram of the mixture of 5 parts by weight of 2-methoxycarbonyl-4-chlorotrifluoromethanesulfonanailide and 15 parts by weight of N-(2-ethylhexyl)bicyclo[2.2.1]hept-5-ene-2,3-dicarboximide were spread on a porous ceramic body (height 4.2 cm, width 4.2 cm, thickness 1.2 cm, pore diameter of 0.3 cm, 102 pores, Kyosera Corporation brand) to gain the insecticidal/acaricidal composition of the present invention (mat formulation for vaporization under heating).

Production Example 4

2-methoxycarbonyl-4-chlorotrifluoromethanesulfonanilide and N-(2-ethylhexyl)bicyclo[2.2.1]hept-5-ene-2,3-dicarboximide were diluted with acetone, then on 1 $m^2$ craft paper 2-methoxycarbonyl-4-clorotrifluoromethanesulfonanilide and N-(2-ethylhexyl)bicyclo[2.2.1]hept-5-ene-2,3-dicarboximide were dropped to become accordingly 0.05 g and 0.8 g, soaked, then dried to gain and the insecticidal/acaricidal composition of the present invention (sheet formulation).

Next, the test examples for the insecticidal/acaricidal composition of the present invention are explained.

Test Example 1

The insecticidal/acaricidal composition gained in production example 4 (12 cm×12 cm) was pasted onto the central region of a venire board (15 cm×15 cm). On top of a carpet cut 3 cm×3 cm, about 200 American house dust mites (*Dermatophagoides pteronyssinus*) bearing 0.1 g powdered animal food was spread and placed on top of the sheet acaricidal/insecticidal composition that was stated above. This was put in a plastic case with an estimated volume of 2.6 L, then a cup holding an aqueous solution saturated with ammonium nitrate was positioned on the bottom of the plastic case for humidity control use, and then closed. Retrieving the carpet six weeks later, an adhesive sheet was stuck onto the carpet surface, then placed this carpet on a hot plate heated up to 60° C. and collected the mites that tried to escape to the upper region with the adhesive sheet, observed the adhesive sheet on a microscope, and determined the number of surviving mites by counting. The number of surviving mites for the non-disposed area and the number of surviving mites for the disposed area quantitated the mite controlling index by means of the equation below.

$$\text{mite controlling index} = \frac{\begin{array}{c}\text{number of surviving mites for the non-disposed area}\end{array} - \begin{array}{c}\text{number of surviving mites for the disposed area}\end{array}}{\text{number of surviving mites for the non-disposed area}} \times 100$$

An extermination sheet preserving either 2-methoxycarbonyl-4-chlorotrifluoromethanesulfonanalide or N-(2-ethylhexyl)bicyclo[2.2.1]hept-5-ene-3-dicarboximide independently and a sheet without the disposal of the active ingredient practiced the same equation.

Resulting, the experiment using the sheet gained in production example 4 had an index of 64.5. However, compared to production example 4, an experiment using a 1 m² sheet preserving 0.05 g of only 2-methoxycarbonyl-4-chlorotrifluoromethanesulfonanilide had an index of 20.3; an experiment using a sheet preserving 0.8 g of only N-(2-ethylhexyl) bicyclo[2.2.11]hept-5-ene-2,3-dicarboximide had an index of 0; therefore, acknowledging that the joining of N-(2-ethylhexyl)bicyclo[2.2.1]hept-5-en-2,3-dicarboxyimide greatly increases the mite controlling effectiveness of 2-methoxycarbonyl-4-chlorotrifluoromethanesulfonanilide.

What is claimed is:

1. An insecticidal/acaricidal composition which comprises synergistic objective amounts of 2-methoxycarbonyl-4-chlorotrifluoromethanesulfonanilide and N-(2-ethylhexyl) bicyclo[2.2.1]hept-5-ene-2,3-dicarboximide as an active ingredient, and inert carrier.

2. The insecticidal/acaricidal composition according to claim 1, wherein the weight ratio between 2-methoxycarbonyl-4-chlorotrifuoromethanesulfonanilide and N-(2-ethylhexyl)bicyclo[2.2.1]hept-5-ene-2,3-dicarboximide is within the range of 1:1 to 1:50.

3. A method for controlling insects/acarina which comprises applying a synergistic effective amount of 2-methoxycarbonyl-4-chlorotrifluoromethanesulfonanilide and N-(2-ethylhexyl)bicyclo [2.2.1]hept-5-ene-2,3-dicarboximide to insects/acarina or the locus they inhabit.

4. The method according to claim 3, wherein the weight ratio between 2-methoxycarbonyl-4-chlorotrifuoromethanesulfonanilide and N-(2-ethylhexyl) bicyclo[2.2.1]hept-5-ene-2,3-dicarboximide is within the range of 1:1 to 1:50.

5. A method for controlling an indoor locus from inhabiting mites which comprises applying to said locus a synergistic effective amount of 2-methoxycarbonyl-4-chlorotrifuoromethanesulfonanilide and N-(2-ethylhexyl) bicyclo[2.2.1]hept-5-ene-2,3-dicarboximide.

6. The method according to claim 5, wherein the weight ratio between 2-methoxycarbonyl-4-chlorotrifuoromethanesulfonanilide and N-(2-ethylhexyl) bicyclo[2.2.1]hept-5-ene-2,3-dicarboximide is within the range of 1:1 to 1:50.

* * * * *